(12) United States Patent
Lang et al.

(10) Patent No.: US 7,175,673 B2
(45) Date of Patent: Feb. 13, 2007

(54) COMPOSITION FOR THE OXIDATION DYEING OF KERATINOUS FIBERS CONTAINING A LACCASE AND DYEING METHOD USING THIS COMPOSITION

(75) Inventors: Gérard Lang, Saint Prix (FR); Jean Cotteret, Verneuil sur Seine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/973,242

(22) Filed: Oct. 27, 2004

(65) Prior Publication Data

US 2005/0066452 A1     Mar. 31, 2005

Related U.S. Application Data

(63) Continuation of application No. 09/600,134, filed as application No. PCT/FR98/02830 on Dec. 22, 1998.

(30) Foreign Application Priority Data

Jan. 13, 1998   (FR)   ................................. 98 00260

(51) Int. Cl.
*A61K 7/13*     (2006.01)

(52) U.S. Cl. ............. 8/405; 8/401; 8/406; 8/407; 8/408; 8/410; 8/411; 8/421

(58) Field of Classification Search ............... 8/401, 8/405, 406, 408, 410, 411, 421, 407
See application file for complete search history.

(56) References Cited

U.S. PATENT DOCUMENTS 5,769,903 A * 6/1998 Audousset et al. ............ 8/409

FOREIGN PATENT DOCUMENTS

WO    WO 97/19999    *    6/1997

\* cited by examiner

*Primary Examiner*—Eisa Elhilo
(74) *Attorney, Agent, or Firm*—Finnegan, Henderson, Farabow, Garrett & Dunner, LLP

(57) ABSTRACT

The invention concerns a ready-to-use composition for oxidation dyeing of keratinous fibres, and in particular human keratinous fibres such as hair comprising, in a medium suitable for dyeing, 3-methyl 4-amino phenol as oxidation base, and at least an enzyme such as laccase, as well as the dyeing method using said composition.

37 Claims, No Drawings

COMPOSITION FOR THE OXIDATION DYEING OF KERATINOUS FIBERS CONTAINING A LACCASE AND DYEING METHOD USING THIS COMPOSITION

This is a continuation application of prior application Ser. No. 09/600,134 filed Sep. 11, 2000 now abandoned of Gerard Lang et al., for KERATINOUS FIBRE OXIDATION DYEING COMPOSITION CONTAINING A LACCASE AND DYEING METHOD USING SAME now abandoned, which is a continuation application of PCT international application no. PCT/FR98/02830, filed Dec. 22, 1998, which claims priority to French application no. 98/00,260, filed Jan. 13, 1998, each of which are incorporated by reference in the instant application.

The subject of the invention is a composition for the oxidation dyeing of keratinous fibers and in particular human keratinous fibers such as hair, comprising, in a medium appropriate for dyeing, 3-methyl-4-aminophenol as oxidation base and at least one enzyme of laccase type, and the dyeing method using this composition.

It is known to dye keratinous fibers, and in particular human hair, with dyeing compositions containing precursors for oxidation dyeing, in particular ortho- and para-phenylenediamines, ortho- or para-aminophenols, heterocyclic bases generally called oxidation bases. The precursors for oxidation dyeing (oxidation bases) are colorless or weakly colored compounds which, combined with oxidizing products, can give rise to dye and colored compounds by a process of oxidative condensation.

It is also known that the shades obtained with these oxidation bases can be varied by combining them with couplers or color modifiers, the latter being chosen in particular from aromatic meta-diamines, meta-aminophenols, meta-diphenols and certain heterocyclic compounds.

The variety of molecules used in oxidation bases an couplers allows a rich palette of colors to be obtained.

The so-called "permanent" color obtained by means of these oxidation dyes should moreover satisfy a number of requirements. Thus, it should have no drawbacks from the toxicological point of view, it should make it possible to obtain shades of the desired intensity and it should exhibit good resistance toward external agents (light, adverse weather conditions, washing, permanent waving, perspiration, rubbing).

The dyes should also make it possible to cover gray hair, and thus should be the least selective possible, that is to say they should make it possible to obtain the smallest possible differences in color all along the same keratinous fiber, which may indeed be differently sensitized (i.e. damaged) between its tip and its root.

The oxidation dyeing of keratinous fibers is generally carried out in an alkaline medium, in the presence of hydrogen peroxide. However, the use of alkaline media in the presence of hydrogen peroxide has the disadvantage of causing substantial degradation of the fibers, as well as decoloring of the keratinous fibers which is not always desirable.

The oxidation dyeing of keratinous fibers can also be carried out with the aid of oxidizing systems different from hydrogen peroxide such as enzymatic systems. Thus, it has already been proposed in Patent U.S. Pat. No. 3,251,742, Patent Applications FR-A-2,112,549 FR-A-2,694,018, EP-A-0,504,005, WO95/07098, WO95/33836, WO95/33837, WO96/00290, WO97/19998 and WO97/19999 to dye keratinous fibers with compositions comprising at least [lacuna] oxidation dye, or at least one melanin precursor, in combination with enzymes of the laccase type, said compositions being brought into contact with atmospheric oxygen. These dyeing formulations, although used under conditions which do not cause degradation of the keratinous fibers comparable to that caused by dyeings carried out in the presence of hydrogen peroxide, lead to colors which are still inadequate both from the point of view of homogeneity of the color distributed along the fiber (unison), from the point of view of chromaticity (luminosity) and of the dyeing power.

In point of fact, the Applicant Company has now just discovered that it is possible to obtain novel dyes, which are capable of resulting in powerful colorings without-causing significant degradation of the keratinous fibers, which exhibit low selectivity and which exhibit good resistance to various attacks to which the fibers may be subjected, by combining 3-methyl-4-aminophenol, as oxidation base, and at least one enzyme of laccase type.

This discovery forms the basis of the present invention.

The first subject of the invention is there fore a ready-to-use composition for the oxidation dyeing of keratinous fibers and in particular human keratinous fibers such as hair, which comprises, in a medium appropriate for dyeing:

3-methyl-4-aminophenol and/or at least one of its addition salts with an acid, as oxidation base, and at least one enzyme of laccase type.

The ready- to-use dyeing composition in accordance with the invention results in powerful colorings which exhibit low selectivity and excellent properties of resistance both with respect to atmospheric agents, such as light and bad weather, and with respect to perspiration and various treatments to which the hair may be subjected (washing, permanent deformation).

The subject of the invention is also a method for the oxidation dyeing of keratinous fibers using this ready-to-use dyeing composition.

3-Methyl-4-aminophenol and/or its addition salt (s) with an acid preferably represent from 0.0005 to 12% approximately of the total weight of the dyeing composition in accordance with the invention and still more preferably from 0.005 to 6% by weight approximately of this weight.

The laccase(s) used in the ready-to-use dye composition in accordance with the invention may be chosen in particular from laccases of plant origin, animal origin, fungal origin (yeasts, molds, fungi) or bacterial origin, organisms which may be of mono- or pluricellular origin. The laccase(s) used in the ready-to-use dyeing composition in accordance with the invention can also be obtained by biotechnology.

Among the laccases of plant origin which can be used according to the invention, there may be mentioned the laccases produced by plants which perform chlorophyll synthesis such as those indicated in Patent Application FR-A-2,694,018.

There may be mentioned, in particular, the laccases present in the extracts of *Anacardiaceae* such as for example the extracts of *Magnifera indica*, *Schinus molle* or *Pleiogynium timoriense*, in the extracts of *Podocarpaceae*, *Rosmarinus off.*, *Solanum tuberosum*, *Iris sp.*, *Coffea sp.*, *Daucus carrota*, *Vinca minor*, *Persea americana*, *Catharenthus roseus*, *Musa sp.*, *Malus pumila*, *Gingko biloba*, *Monotropa hypopithys* (Indian pipe), *Aesculus sp.*, *Acer pseudoplatanus*, *Prunus persica* and *Pistacia palaestina*.

Among the laccases of fungal origin optionally obtained by biotechnology which can be used according to the invention, there may be mentioned the laccase(s) derived from *Polyporus versicolor*, *Rhizoctonia practicola* and *Rhus vernicifera* such as described, for example, in Patent Applications FR-A-2,112,549 and EP-A-504005, the laccases described in Patent Applications WO95/07988, WO95/33836, WO95/33837, WO96/00290, WO97/19998 and WO97/19999, whose content is an integral part of the present description, such as for example the laccase(s) derived from *Scytalidium, Polyporus pinsitus, Myceliophtora thermophila, Rhizoctonia solani, Pyricularia orizae*, or variants thereof. There may also be mentioned the laccase(s) derived from *Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporiodes, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants thereof.

The laccases of fungal origin optionally obtained by biotechnology will be preferably chosen.

The enzymatic activity of the laccases used in accordance with the invention and which have syringaldazine among their substrates can be defined from the oxidation of syringaldazine under aerobic conditions. The Lacu unit corresponds to the quantity of enzyme catalyzing the conversion of 1 mmol of syringaldazine per minute at a pH of 5.5 and at a temperature of 30° C. The unit U corresponds to the quantity of enzyme producing a delta absorbance of 0.001 per minute, at a wavelength of 530 nm, using syringaldazine as substrate, at 30° C. and at a pH of 6.5. The enzymatic activity of the laccases of the invention can also be defined from the oxidation of para-phenylenediamine. The ulac unit corresponds to the quantity of enzyme producing a delta absorbance of 0.001 per minute, at a wavelength of 496.5 nm, using para-phenylenediamine as substrate (64 mM) at 30° C. and at a pH of 5.

According to the invention, it is preferable to determine the enzymatic activity in ulac units.

According to a preferred embodiment, the dyeing composition in accordance with the invention also contains one or more couplers, so as to modify or to enrich with highlights the shades obtained by using 3-methyl-4-aminophenol.

The couplers which can be used in the dyeing composition in accordance with the invention can be chosen from the couplers conventionally used in oxidation dyeing and among which may in particular be mentioned meta-phenylenediamines, meta-aminophenols, meta-diphenols and heterocyclic couplers.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-N-(β-hydroxyethyl)amino-1-methoxybenzene, 1,3-diaminobenzene, 1,3-bis(2,4-diaminophenoxy) propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazole-5-one, 1-phenyl-3-methylpyrazole-5-one, 2,6-dimethyl-pyrazolo[1,5-b]-1,2,4-triazole, 2,6-dimethyl[3,2-c]-1,2,4-triazole, 6-methylpyrazolo[1,5-a]benzimidazole, and their addition salts with an acid.

When they are present, the coupler (s) preferably represent from 0.0001 to 8% by weight approximately of the total weight of the dyeing composition, and still more preferably from 0.005 to 5% by weight approximately of this weight.

The dyeing composition in accordance with the invention can also contain, in addition to the 3-methyl-4-aminophenol and/or its addition salts with an acid, at least one additional oxidation base which can be chosen from oxidation bases conventionally used for oxidation dyeing. They can be chosen in particular from para-phenylenediamines, double bases, para-aminophenols, ortho-aminophenols and heterocyclic oxidation bases.

Among the para-phenylenediamines, there may be mentioned more particularly by way of example para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylene-diamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines mentioned hereinabove, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

Among the bisphenylalkylenediamines, there may be mentioned more particularly by way of example N,N'-bis (β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-teramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among the para-aminophenols, there may be mentioned more particularly by way of example para-aminophenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols, there may be mentioned more particularly by way of example 2-aminophenol, 2-amino-5-methylphenol, 2-amino-6-methylphenol, 5-acetamido-2-aminophenol, and their addition salts with an acid.

Among the heterocyclic bases, there may be mentioned more particularly by way of example pyridine derivatives, pyrimidine derivatives and pyrazole derivatives.

When they are used, the additional oxidation base(s) preferably represent from 0.0005 to 12% by weight approximately of the total weight of the dyeing composition in accordance with the invention and still more preferably from 0.005 to 6% by weight approximately of this weight.

In general, the addition salts with an acid which can be used in the context of the dyeing compositions of the invention (oxidation bases and couplers) are in particular chosen from hydrochlorides, hydrobromides, sulfates and tartrates, lactates and acetates.

The dyeing composition in accordance with the invention may also contain one or more direct dyes.

The medium appropriate for dyeing (or carrier) of the ready-to-use dyeing composition in accordance with the invention generally consists of water or of a mixture of water and of at least one organic solvent in order to solubilize the compounds which might not be sufficiently soluble in water.

The pH of the ready-to-use composition in accordance with the invention is chosen such that the enzymatic activity of the laccase is sufficient. It is generally of between 4 and 11 approximately, and preferably between 6 and 9 approximately. It can be adjusted to the desired value by means of acidifying or basifying agents commonly used in dyeing keratinous fibers.

The ready-to-use dyeing composition in accordance with the invention may also contain various adjuvants conventionally used in compositions for dyeing hair, such as anionic, cationic, nonionic, amphoteric or zwitterionic surfactants or mixtures thereof, polymers, antioxidants, enzymes different from the laccases used in accordance with the invention, such as for example peroxidases or oxidoreductases containing 2 electrons, penetrating agents, sequestering agents, perfumes, buffers, dispersing agents, thickeners, film-forming agents, preservatives, opacifying agents or vitamins.

Of course, persons skilled in the art will be careful to choose this or these optional additional compounds such that the advantageous properties intrinsically attached to the ready-to-use dyeing composition in accordance with the invention are not, or substantially not, impaired by the addition (s) envisaged.

The ready-to-use dyeing composition in accordance with the invention can be provided in various forms, such as in the form of liquids, creams, gels, optionally pressurized, or in any other form appropriate for dyeing keratinous fibers, in particular human hair. In this case, the 3-methyl-4-aminophenol and, if appropriate, the additional oxidation dyes and the enzyme(s) of laccase type are present in the same ready-to-use composition, and consequently said composition should be free of gaseous oxygen, so as to avoid any premature oxidation of the oxidation dye(s).

The subject of the invention is also a method of dyeing keratinous fibers, and in particular human keratinous fibers such as hair, using the ready-to-use dyeing composition as defined above.

According to this method, at least one ready-to-use dyeing composition as defined above is applied to the fibers for a sufficient time to develop the desired color, after which they are rinsed, optionally washed with shampoo, rinsed again and dried.

The time necessary for the development of the color on the keratinous fibers is generally between 3 and 60 minutes and still more precisely 5 and 40 minutes.

According to one particular embodiment of the invention, the method comprises a preliminary step consisting in storing in a separate form, on the one hand, a composition (A) comprising, in a medium appropriate for dyeing, 3-methyl-4-aminophenol and/or at least one of its addition salts with an acid and, on the other hand, a composition (B) containing, in a medium appropriate for dyeing, at least one enzyme of laccase type, and then in mixing them at the time of use before applying this mixture to the keratinous fibers, Another subject of the invention is a multi-compartment device or dyeing (kit) or any other multi-compartment packaging system in which a first comparment contains the composition (A) as defined above and a second compartment contains a composition (B) as defined above. These devices may be equipped with a means which makes it possible to deliver the desired mixture to the hair, such as the devices described in Patent FR-2,586,913 in the name of the applicant.

The following examples are intended to illustrate the invention without, however, limiting the scope thereof.

DYEING EXAMPLE

The following dyeing composition was prepared:

| | |
|---|---|
| 3-Methyl-4-aminophenol | 0.25 g |
| 5-N-(β-Hydroxyethyl)amino-2-methylphenol | 0.30 g |
| Laccase obtained from *Rhus vernicifera* containing 180 units/mg sold by the company ICN | 1.8 g |
| ($C_8$–$C_{10}$)Alkyl polyglucoside in aqueous solution containing 60% of active substance (A.S.), sold under the name ORAMIX CG110 ® by the company SEPPIC | 8.0 g |
| Ethanol | 20 g |
| pH agent | q.s. pH 6.5 |
| Demineralized water | q.s. for 100 g |

The ready-to-use dyeing composition described above was applied to locks of natural gray hair which is 90% white for 40 minutes at a temperature of 30° C. The hair was then rinsed and then dried.

The hair was dyed in a coppery gold shade.

In the dyeing composition described above, the Rhus vernicifera laccase at 180 units/mg, sold by the company Sigma, can be replaced by 1.0 g of Pyricularia orizae laccase at 100 units/mg sold by the company ICN.

The invention claimed is:

1. A composition for the oxidation dyeing of keratinous fibers comprising:
   (a) at least one oxidation base chosen from 3-methyl-4-aminophenol and the acid addition salts of said at least one oxidation base; and
   (b) at least one enzyme of laccase type.

2. A composition according to claim 1, wherein said keratinous fibers are human keratinous fibers.

3. A composition according to claim 2, wherein said human keratinous fibers are hair.

4. A composition according to claim 1, wherein said at least one oxidation base is present in a concentration ranging from 0.0005% to 12% by weight of the total weight of said composition.

5. A composition according to claim 4, wherein said at least one oxidation base is present in a concentration ranging from 0.005% to 6% by weight of the total weight of said composition.

6. A composition according to claim 1, wherein said at least one enzyme of laccase type is chosen from laccases of plant origin, animal origin, fungal origin and bacterial origin and laccases obtained by biotechnology.

7. A composition according to claim 1, wherein said at least one enzyme of laccase type is chosen from those extracted from plants chosen from *Anacardiaceae, Podocarpaceae, Rosmarinus off., Solanum tuberosum, Iris sp., Coffea sp., Daucus carrota, Vinca minor, Persea americana, Catharenthus roseus, Musa sp., Malus pumila, Gingko biloba, Monotropa hypopithys, Aesculus sp., Acer pseudoplatanus, Prunus persica* and *Pistacia palaestina*.

8. A composition according to claim 6, wherein said at least one enzyme of laccase type is chosen from laccases of microbial origin and laccases obtained by biotechnology.

9. A composition according to claim 1, wherein said at least one enzyme of laccase type is chosen from laccases derived from fungi chosen from *Polyporus versicolor, Rhizoctonia praticola, Rhus vernicifera, Scytalidium, Polyporus pinsitus, Myceliophtora thermophila, Rhizoctonia solani, Pyricularia orizae, Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants of all said fungi.

10. A composition according to claim 1, further comprising at least one coupler chosen from meta-phenylenediamines, meta-aminophenols, meta-diphenols, heterocyclic couplers and the acid addition salts of all said couplers.

11. A composition according to claim 10, wherein said at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-N-(β-hydroxyethyl) amino-1-methoxybenzene, 1,3-diaminobenzene, 1,3-bis(2, 4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazole-5-one, 1-phenyl-3-methylpyrazole-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole and the acid addition salts of all said couplers.

12. A composition according to claim 10, wherein said at least one coupler is present in a concentration ranging from 0.0001% to 8% by weight of the total weight of said composition.

13. A composition according to claim 12, wherein said at least one coupler is present in a concentration ranging from 0.005% to 5% by weight of the total weight of said composition.

14. A composition according to claim 1, further comprising at least one additional oxidation base chosen from para-phenylenediamines, double bases, para-aminophenols, ortho-aminophenols, heterocyclic oxidation bases and the acid addition salts of all said additional oxidation bases.

15. A composition according to claim 14, wherein said at least one additional oxidation base is present in a concentration ranging from 0.0005% to 12% by weight of the total weight of said composition.

16. A composition according to claim 15, wherein said at least one additional oxidation base is present in a concentration ranging from 0.005% to 6% by weight of the total weight of said composition.

17. A composition according to claim 1, wherein said acid addition salts are chosen from hydrochlorides, hydrobromides, sulfates and tartrates, lactates and acetates.

18. A composition according to claim 10, wherein said acid addition salts are chosen from hydrochlorides, hydrobromides, sulfates and tartrates, lactates and acetates.

19. A composition according to claim 14, wherein said acid addition salts are chosen from hydrochlorides, hydrobromides, sulfates and tartrates, lactates and acetates.

20. A composition according to claim 1, further comprising a medium appropriate for dyeing.

21. A composition according to claim 20, wherein said medium appropriate for dyeing is chosen from water and at least one organic solvent.

22. A composition according to claim 1 having a pH ranging from about 4 to about 11.

23. A composition according to claim 22, wherein said pH ranges from about 6 to about 9.

24. A composition according to claim 1, wherein said composition is a ready-to-use composition.

25. A composition according to claim 1, further comprising at least one direct dye.

26. A composition according to claim 1, further comprising at least one suitable additive chosen from anoinic surfactants, cationic surfactants, nonionic surfactants, amphoteric surfactants, zwitterionic surfactants, polymers, antioxidants, enzymes different from said at least one enzyme of laccase type as defined in claim 1, penetrating agents, sequestering agents, perfumes, buffers, dispersing agents, thickeners, film-forming agents, preservatives, opacifying agents and vitamins.

27. A composition according to claim 1 in the form of a liquid, a cream, a gel or in any other form appropriate for keratinous fibers.

28. A composition according to claim 27, wherein said composition form may optionally be pressurized.

29. A method for dyeing keratinous fibers comprising the step of applying a ready-to-use composition to said fibers for a time sufficient to achieve a desired colouration, wherein said ready-to-use composition comprises:
  (a) at least one oxidation base chosen from 3-methyl-4-aminophenol and the acid addition salts of said at least one oxidation base; and
  (b) at least one enzyme of laccase type.

30. A method according to claim 29, further comprising the step of rinsing said composition from said fibers.

31. A method according to claim 30, further comprising the step of washing the fibers.

32. A method according to claim 31, further comprising the step of rinsing said fibers a second time.

33. A method according to claim 32, further comprising the step of drying said fibers.

34. A method according to claim 29, wherein said time sufficient to achieve a desired colouration ranges from 3 to 60 minutes.

35. A method according to claim 34, wherein said time sufficient to achieve a desired colouration ranges from 5 to 40 minutes.

36. A method for dyeing keratinous fibers comprising the steps of:
  (a) storing a first composition,
  (b) storing a second composition separately from said first composition, (c) mixing the first composition with the second composition to form a mixture, and
(d) applying said mixture to said keratinous fibers for a time sufficient to achieve a desired colouration,
wherein said first composition comprises at least one oxidation base chosen from 3-methyl-4-aminophenol and the acid addition salts of said at least one oxidation base in a medium appropriate for keratinous fibers, and
wherein said second composition comprises at least one enzyme of the laccase type in a medium appropriate for keratinous fibers.

37. A multicompartment device or dyeing kit, wherein said device or kit comprises:

(a) a first compartment comprising a first composition, and
(b) a second compartment comprising a second composition,
wherein said first compartment comprises at least one oxidation base chosen from 3-methyl-4-aminophenol and the acid addition salts of said at least one oxidation base in a medium appropriate for keratinous fibers, and
wherein said second compartment comprises at least one enzyme of the laccase type in a medium appropriate for keratinous fibers.

* * * * *